(12) United States Patent
Li et al.

(10) Patent No.: US 11,456,078 B2
(45) Date of Patent: Sep. 27, 2022

(54) MULTI-CENTER SYNERGETIC CANCER PROGNOSIS PREDICTION SYSTEM BASED ON MULTI-SOURCE MIGRATION LEARNING

(71) Applicant: ZHEJIANG LAB, Hangzhou (CN)

(72) Inventors: Jingsong Li, Hangzhou (CN); Yu Tian, Hangzhou (CN); Weiguo Chen, Hangzhou (CN); Jing Ma, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 17/543,738

(22) Filed: Dec. 7, 2021

(65) Prior Publication Data
US 2022/0093258 A1  Mar. 24, 2022

Related U.S. Application Data

(63) Continuation of application No. PCT/CN2021/071827, filed on Jan. 14, 2021.

(51) Int. Cl.
*G16H 50/20* (2018.01)
*G16H 40/20* (2018.01)
(Continued)

(52) U.S. Cl.
CPC ........... *G16H 50/20* (2018.01); *A61B 5/7275* (2013.01); *G16H 10/60* (2018.01); *G16H 40/20* (2018.01); *G16H 50/70* (2018.01)

(58) Field of Classification Search
CPC ........ G16H 50/20; G16H 40/20; G16H 10/60; G16H 50/70; A61B 5/7275
See application file for complete search history.

(56) References Cited

U.S. PATENT DOCUMENTS

2019/0295252 A1* 9/2019 Fuchs .................... G16H 30/40
2019/0316209 A1* 10/2019 Hubbell ............... C12Q 1/6806
(Continued)

FOREIGN PATENT DOCUMENTS

| CN | 106897545 A | 6/2017 |
|----|-------------|--------|
| CN | 108520780 A | 9/2018 |

(Continued)

OTHER PUBLICATIONS

International Search Report (PCT/CN2021/071827); dated Apr. 2, 2021.

(Continued)

*Primary Examiner* — Mark Holcomb
(74) *Attorney, Agent, or Firm* — W&G Law Group

(57) ABSTRACT

Provided is a multi-center synergetic cancer prognosis prediction system based on multi-source migration learning. The system includes a model parameter setting module, a data screening module, and a multi-source migration learning module, wherein the model parameter setting module is responsible for setting cancer prognosis prediction model parameters; the data screening module is arranged in a clinical center, and a management center transmits the set model parameter to each clinical center, such that each clinical center inquires a sample feature and prognosis index data from a local database according to the model parameter, so as to preprocess the data; and the multi-source migration learning module includes a source model training unit, a migration weight calculation unit, and a target model calculation unit.

6 Claims, 2 Drawing Sheets

(51) Int. Cl.
*G16H 10/60* (2018.01)
*G16H 50/70* (2018.01)
*A61B 5/00* (2006.01)

(56) References Cited

U.S. PATENT DOCUMENTS

| | | | |
|---|---|---|---|
| 2020/0126636 A1* | 4/2020 | Yu | G16H 50/30 |
| 2020/0219587 A1* | 7/2020 | Hubbell | G16B 40/30 |
| 2020/0258601 A1* | 8/2020 | Lau | G16B 30/10 |
| 2021/0090694 A1* | 3/2021 | Colley | G16B 40/00 |
| 2021/0169349 A1* | 6/2021 | Madabhushi | A61B 6/502 |
| 2021/0249132 A1* | 8/2021 | Colborn | G16H 20/00 |

FOREIGN PATENT DOCUMENTS

| | | |
|---|---|---|
| CN | 108922628 A | 11/2018 |
| CN | 109902421 A | 6/2019 |
| CN | 110391022 A | 10/2019 |
| CN | 111261299 A | 6/2020 |
| WO | 2018143540 A1 | 8/2018 |

OTHER PUBLICATIONS

Multi-Source Domain Adaptation and Its Application to Early Detection of Fatigue; Date of Mailing: Dec. 31, 2011.
A Disease Prediction Model Based on Dynamic Sampling and Transfer Learning; Date of Mailing: Dec. 31, 2019.

\* cited by examiner

MULTI-CENTER SYNERGETIC CANCER PROGNOSIS PREDICTION SYSTEM BASED ON MULTI-SOURCE MIGRATION LEARNING

CROSS-REFERENCE TO RELATED APPLICATIONS

The present application is a continuation of International Application No. PCT/CN2020/071827, filed on Jan. 14, 2021, which claims priority to Chinese Application No. 202010038230.2, filed on Jan. 14, 2020, the contents of both of which are incorporated herein by reference in their entireties.

TECHNICAL FIELD

The present application belongs to the medical field and the machine learning field, and particularly relates to a multi-center synergetic cancer prognosis prediction system based on multi-source migration learning.

BACKGROUND

The mortality of cancer is high, and with its rising incidence, cancer has become one of the main causes of human death. High-quality cancer prognosis prediction can provide basis for doctors' clinical decision-making, and is of great significance for cancer control and treatment.

Traditional prognosis prediction is based on clinical experience of an expert (e.g., a TNM model), and lacks evidence-based support. With the development of medical information technology, especially an electronic medical record, medical big data analysis and mining, and the like techniques, a data-driven prognosis prediction model has attracted more and more attention. These prediction models require large-scale clinical data, but are directed to a single disease, and a single institution often lacks enough label data to support model training, so that the model effect is poor. Therefore, it needs to construct a prognosis prediction model through multi-center synergy.

An existing technical solution generally summarizes the data of multiple institutions and then train a general model. Because of the heterogeneity of data among different institutions (mainly embodied in marginal distribution and conditional probability distributional difference), the generalization ability of the general model obtained by training is poor. When the data of a target institution is highly heterogeneous with the training data, the model often does not perform well. Only after a certain number of labeled samples have been accumulated in the target institution, a better performance can be obtained by calibrating the general model with local labeled samples. Currently, there is still lack of a mechanism to integrate model training with an application environment.

Whether training the model directly with the local labeled samples or correcting the general model with the local labeled samples, there are certain requirements for the number of the local labeled samples. In the absence of a local label, an existing method is difficult to apply. Furthermore, large-scale data needs mutual participation of multiple institutions, and there is a risk of patient privacy leakage.

SUMMARY

An objective of the present application is to provide a multi-center synergetic cancer prognosis prediction system based on multi-source migration learning aiming at the shortcomings of the prior art, which mainly solves the following technical problems:

1. the data resources of electronic medical records in a single institution are limited, and although the patient scale and the total amount of medical record data are large, the number of patients with clear prognosis outcome events (such as death, recurrence, etc.) in the single institution is limited for the requirements of prognosis research of a specific disease, thereby limiting the construction of a high-quality prognosis prediction model for the specific disease;

2. there is a lack of research on the generalization ability of a model, the model constructed by an existing method (especially a statistical model) can get better prediction performance on a data set with similar feature distribution to a training data set, but it often does not perform well on a data set with marginal probability distribution and conditional probability distributional difference different from a training environment.

The objective of the present application is realized by the following technical solutions: a multi-center synergetic cancer prognosis prediction system based on multi-source migration learning, which includes a model parameter setting module, a data screening module, and a multi-source migration learning module, the model parameter setting module is arranged at a management center and is responsible for setting cancer prognosis prediction model parameters, including a cancer category (e.g., colorectal cancer), a source center and a target center, sample characteristics (e.g., age, sex, colorectal cancer grading, histological classification, etc.), a sample data preprocessing method, and a prognosis index (e.g., five-year survival state);

the management center performs coordination management of resources of each clinical center and accepts access of a user;

the source center is a clinical center with labeled samples for a specific cancer category, and is responsible for the training of a source cancer prognosis prediction model;

the target center is a clinical center with unlabeled samples for a specific cancer category, and is responsible for training a target cancer prognosis prediction model;

the clinical center is an institution that actually holds clinical data, and is responsible for screening sample data and training a cancer prognosis prediction model, the data screening module is arranged at a clinical center, the management center transmits the set model parameter to each clinical center, such that each clinical center screens data by utilizing the data screening module, inquires a sample feature and prognosis index data from the local database of the clinical center according to the model parameter, and preprocesses the sample data according to a set sample data preprocessing method, so that the source center obtains a labeled sample set and the target center obtains an unlabeled sample set.

the multi-source migration learning module includes a source model training unit, a migration weight calculation unit, and a target model calculation unit;

the source model training unit is arranged at each source center, it is assumed that there are K source centers denoted by $S_1, S_2, S_3 \ldots S_K$, and an $i^{th}$ source center trains a local source cancer prognosis prediction model $f^{S_i}(\bullet)$ through its source model training unit and transmits the trained source model back to the management center;

the migration weight calculation unit is arranged at the target center, and receives the K source cancer prognosis prediction models sent by the management center, it is assumed that there are $n_T$ unlabeled samples at the target center, an $i^{th}$ unlabeled sample is expressed as $x_i^T$, the K source cancer prognosis prediction models are respectively utilized to perform prognosis prediction of the sample $x_i^T$ to obtain a prediction label vector $H_i^S$:

$$H_i^S = [f^{S_1}(x_i^T), f^{S_2}(x_i^T), \ldots, f^{S_K}(x_i^T)]$$

weighted summation is performed on the K prediction labels in the prediction label vector $H_i^S$ to obtain a pseudo label $\hat{y}_i^T$ of the sample $x_i^T$:

$$\hat{y}_i^T = H_i^S \theta = \sum_{j=1}^{K} \theta^{S_j} f^{S_j}(x_i^T)$$

where $\theta = [\theta^{S_1}, \theta^{S_2}, \theta^{S_3} \ldots \theta^{S_K}]^T$ represents the migration weight of each source model, the weight that minimizes the difference between two samples in the target center sample set can be sought based on a smoothness assumption on the sample data of the target center, which is expressed as the following optimization problem:

$$\min_{\theta:\theta'e=1, \theta \geq 0} \sum_{i,j=1}^{n_T} (H_i^S \theta - H_j^S \theta)^2 W_{ij}$$

where $\theta'$ is a transposition of $\theta$, e is a unit vector, and $W_{ij}$ indicates the similarity among the samples;

the aforementioned optimization problem is transformed into:

$$\min_{\theta:\theta'e=1, \theta \geq 0} \theta' H^{S'} L^T H^S \theta$$

where $H^S$ is a $n_T \times K$ matrix, and $L^T$ represents a graph Laplacian operator related to the target center, which can be obtained by calculating according to $L^T = D - W$, where W is a similarity matrix of the samples of the target center, and D is a diagonal matrix obtained by calculating according to $D_{ii} = \Sigma_{j=1}^{n_T} W_{ij}$;

therefore, the optimization problem is transformed into a standard quadratic programming problem, which is solved to obtain a migration weight $\theta$;

the target model calculation unit is arranged at the target center, obtains a sample pseudo label according to the migration weight $\theta$, trains the target cancer prognosis prediction model at the target center by utilizing the pseudo label, and transmits the trained target model back to the management center.

Further, the system further includes a model application module, which is arranged at the management center, receives the sample feature input by a user when setting the model parameter, calls the target model to perform cancer prognosis prediction, and presents a prediction result to the user, wherein the presentation mode can be a numerical value, a table, a graph, etc.

Further, the cancer prognosis prediction model can adopt a logistic regression model, a support vector machine model, a decision tree model, a neural network model, and the like.

Further, the similarity $W_{ij}$ among the samples can be cosine similarity, Gaussian similarity, etc.

Further, the sample data preprocessing method includes missing value processing, dummy variable processing, normalization processing, and the like. Further, the sample feature includes demographic information, physiological parameters and cancer pathological examination information (e.g., age, sex, colorectal cancer grading, histological classification, etc.) extracted from an electronic medical record of a patient.

The beneficial effects of the present application are that: the present application utilizes multi-source migration learning to solve the problem of heterogeneity of data between the source center and the target center and utilizes multi-source migration learning to solve the problem of insufficient label data at the target center, which makes it possible to construct a more accurate prediction model on the premise of taking the heterogeneity of data from multiple centers into consideration. Meanwhile, complementation and sharing of original data from all institutions during a model training process are realized, thereby avoiding leakage of patient privacy.

DESCRIPTION OF EMBODIMENTS

The present application will be described in further detail below with reference to the accompanying drawings and specific examples.

Figure 1:
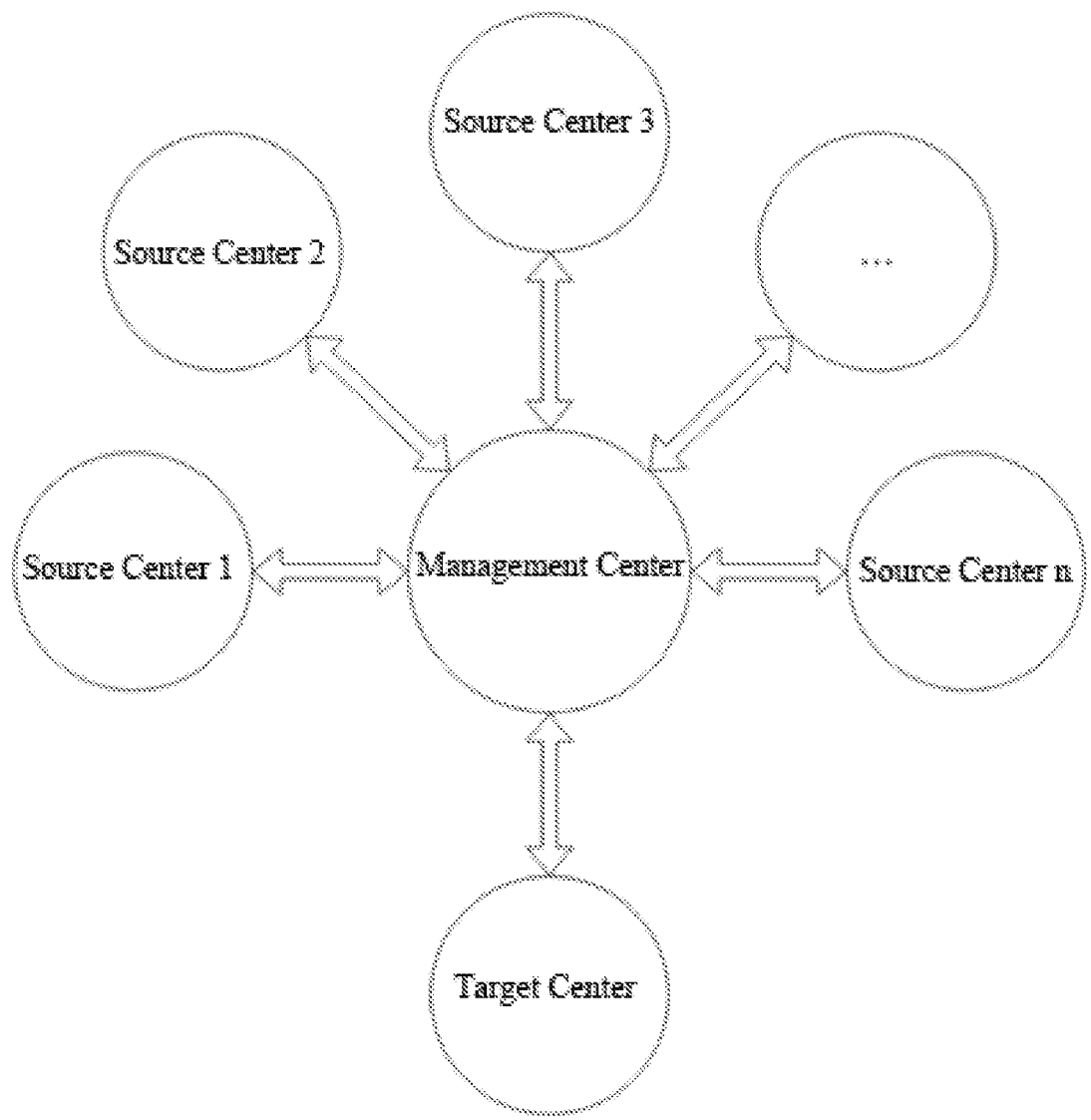
FIG. 1 is a system distribution frame diagram of the present application.
Figure 2:
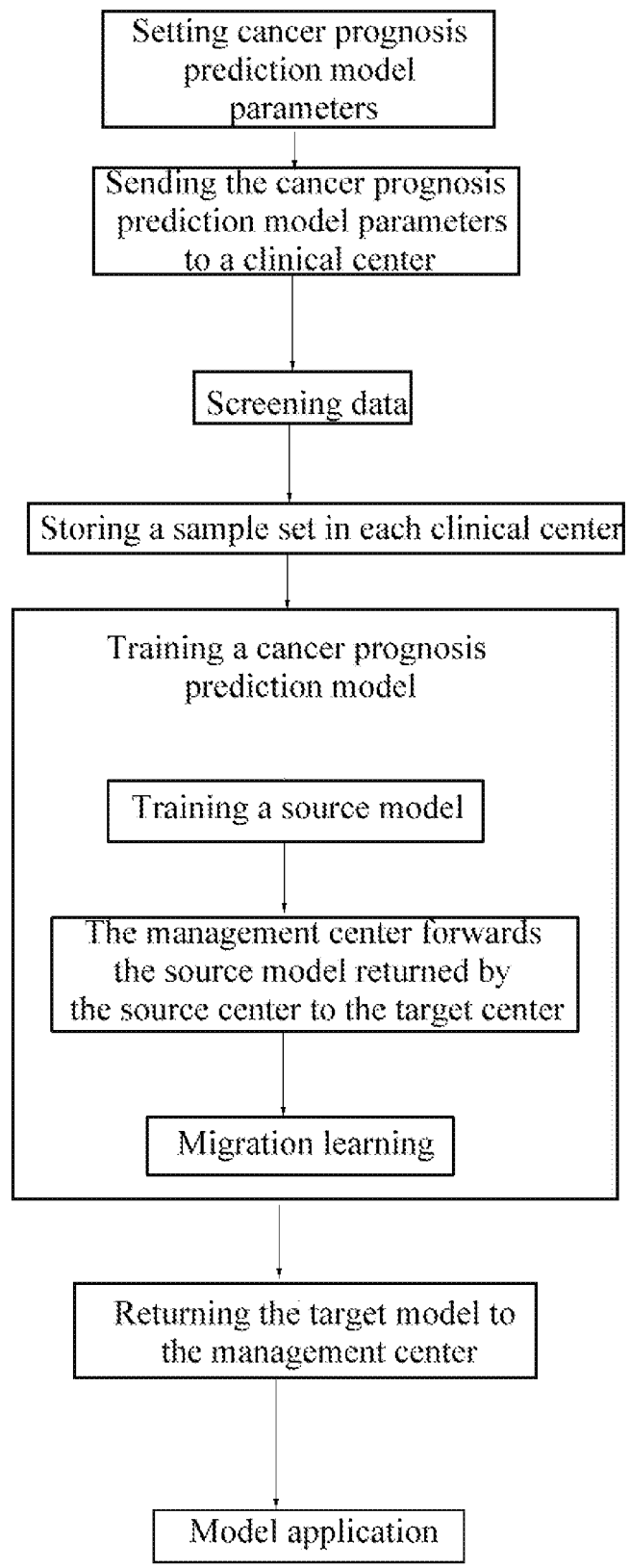
FIG. 2 is a data flow diagram: a rounded rectangle represents the operation of the management center, and the right rectangle represents the operation of the clinical center.

As shown in FIG. 1, the present application provides a multi-center synergetic cancer prognosis prediction system based on multi-source migration learning, which includes a model parameter setting module, a data screening module, and a multi-source migration learning module, the model parameter setting module is arranged at the management center and is responsible for setting cancer prognosis prediction model parameters, in this example the cancer category is set as colorectal cancer, 4 source centers are set as $S_1, S_2, S_3, S_4$ respectively, the target center is set as T, the sample feature is set as age, sex, colorectal cancer grading, histological classification, the number of positive lymph nodes, the size of a cancer tissue and platelet count, the sample data preprocessing method is set to perform mean filling on all sample feature missing values and perform dummy variable processing of the classification feature in the sample feature, and the prognosis index is set as a five-year survival state.

the management center performs coordination management of resources of each clinical center and accepts access of a user;

the source center is a clinical center with labeled samples for a specific cancer category, and is responsible for the training of a source cancer prognosis prediction model;

the target center is a clinical center with unlabeled samples for a specific cancer category, and is responsible for training a target cancer prognosis prediction model;

the clinical center is an institution that actually holds clinical data, and is responsible for screening sample data and training a cancer prognosis prediction model;

the cancer prognosis prediction model in this example is a logistic regression model:

$$\hat{p} = f(X) = \frac{\exp(\beta X)}{1 + \exp(\beta X)}$$

where β is a model coefficient, X is a sample feature vector, and $\hat{p}$ is a prediction result, the data screening module is arranged at a clinical center, the management center transmits the set model parameter to each clinical center, such that each clinical center screens data by utilizing the data screening module, inquires a sample feature and prognosis index data from the local database of the clinical center according to the model parameter, and preprocesses the sample data according to a set sample data preprocessing method, so that the source center obtains a labeled sample set and the target center obtains an unlabeled sample set;

the multi-source migration learning module includes a source model training unit, a migration weight calculation unit, and a target model calculation unit;

the source model training unit is arranged at each source center, it is assumed that 4 source centers are denoted by $S_1, S_2, S_3, S_4$, and the $i^{th}$ source center trains a local source cancer prognosis prediction model $f^{S_i}(\cdot)$ through its source model training unit and transmits the trained source model back to the management center;

the migration weight calculation unit is arranged at the target center, and receives the 4 source cancer prognosis prediction models sent by the management center, it is assumed that there are 936 unlabeled samples at the target center, the $i^{th}$ unlabeled sample is expressed as $x_i^T$, the 4 source cancer prognosis prediction models are respectively utilized to perform prognosis prediction of the sample $x_i^T$ to obtain a prediction label vector $H_i^S$:

$$H_i^S = [f^{S_1}(x_i^T), f^{S_2}(x_i^T), f^{S_3}(x_i^T), f^{S_4}(x_i^T)]$$

weighted summation is performed on the 4 prediction labels in the prediction label vector $H_i^S$ to obtain a pseudo label $\hat{y}_i^T$ of the sample $x_i^T$:

$$\hat{y}_i^T = H_i^S \theta = \sum_{j=1}^{4} \theta^{S_j} f^{S_j}(x_i^T)$$

where $\theta = [\theta^{S_1}, \theta^{S_2}, \theta^{S_3}, \theta^{S_4}]^T$ represents the migration weight of each source model, the weight that minimizes the difference between two samples in the target center sample set can be sought based on a smoothness assumption on the sample data of the target center (the distance among the pseudo labels is smaller when the similarity among the samples is greater), which is expressed as the following optimization problem:

$$\min_{\theta: \theta' e = 1, \theta \geq 0} \sum_{i,j=1}^{936} (H_i^S \theta - H_j^S \theta)^2 W_{ij}$$

wherein θ' is a transposition of θ, e is a unit vector, and $W_{ij}$ indicates the similarity among the samples and is calculated by cosine similarity;

the aforementioned optimization problem is transformed into:

$$\min_{\theta: \theta' e = 1, \theta \geq 0} \theta' H^{S'} L^T H^S \theta$$

where $H^S$ is a 936×4 matrix, and $L^T$ represents a graph Laplacian operator related to the target center, which can be obtained by calculating according to $L^T = D - W$, where W is a similarity matrix of the samples of the target center, and D is a diagonal matrix obtained by calculating according to $D_{ii} = \Sigma_{j=1}^{936} W_{ij}$;

therefore, the optimization problem is transformed into a standard quadratic programming problem, which is solved to obtain a migration weight θ;

the target model calculation unit is arranged at the target center, obtains a sample pseudo label according to the migration weight θ, trains the target cancer prognosis prediction model at the target center by utilizing the pseudo label, and transmits the trained target model back to the management center.

In this example, the model application module is arranged at the management center, receives the data of age, sex, colorectal cancer grading, histological classification, number of positive lymph nodes, size of cancer tissue and platelet count as input by the user when setting the model parameter, calls the target model to perform cancer prognosis prediction, and presents the predicted five-year survival state to the user.

The migration learning in the present application is mainly put forward to break through the assumed limitation that the original machine learning method needs to have the same feature space and the same distribution for model training and data testing. The system of the present application utilizes the multi-source migration learning to solve the problem of insufficient generalization ability of the model when there is difference between the multi-source data set for training the prediction model and the target data set for model application (edge difference, and probability distribution difference).

The aforementioned is only an implementation example of the present application, and is not intended to limit the claimed scope of the present application. Any modifications, equivalent substitutions, improvements, etc. made without creative labor within the spirit and scope of the present application should be included within the claimed scope of the present application.

What is claimed is:

1. A multi-center synergetic cancer prognosis prediction system based on multi-source migration learning, comprising a model parameter setting process, a data screening terminal, and a multi-source migration learning processor wherein the model parameter setting process is arranged at a management center and is configured to set cancer prognosis prediction model parameters by a central processor, comprising a cancer category, a source center and a target center, sample characteristics, a sample data preprocessing method, and a prognosis index;

the management center performs coordination management of resources of all clinical centers and accepts access of a user;

the source center is one or more clinical centers with labeled samples for a specific cancer category, and is responsible for training of a source cancer prognosis prediction model;

the target center is a clinical center with unlabeled samples for a specific cancer category, and is responsible for training a target cancer prognosis prediction model;

the clinical center is one or more institutions that actually holds clinical data, and is responsible for screening sample data and training a cancer prognosis prediction model;

the data screening terminal is arranged at a clinical center, the management center transmits a set model parameter to each of the clinical centers by a signal transmitter, each of the clinical centers screens data by utilizing the data screening terminal, inquires a sample feature and prognosis index data from a local database of the clinical center according to the model parameter, and preprocesses sample data according to a set sample data preprocessing method, and the source center obtains a labeled sample set and the target center obtains an unlabeled sample set;

the multi-source migration learning processor comprises a source model training unit, a migration weight calculation unit, and a target model calculation unit;

the source model training unit is arranged at each source center, it is assumed that there are K source centers denoted by $S_1, S_2, S_3 \ldots S_K$, and a terminal processor of an $i^{th}$ source center trains a local source cancer prognosis prediction model $f^{S_i}(\bullet)$ through its source model training unit and transmits a trained source model back to the management center by the signal transmitter;

the migration weight calculation unit is arranged at the target center, and a terminal process of the target center receives the K source cancer prognosis prediction models sent by the management center by a signal receiver, it is assumed that there $n_T$ unlabeled samples at the target center, an $i^{th}$ unlabeled sample is expressed as $x_i^T$, the K source cancer prognosis prediction models are utilized to perform prognosis prediction of the sample $x_i^T$, respectively, to obtain a prediction label vector $H_i^S$:

$$H_i^S = [f^{S_1}(x_i^T), f^{S_2}(x_i^T), \ldots, f^{S_K}(x_i^T)]$$

weighted summation is performed on the K prediction labels in the prediction label vector $H_i^S$ to obtain a pseudo label $\hat{y}_i^T$ of the sample $x_i^T$:

$$\hat{y}_i^T = H_i^S \theta = \sum_{j=1}^{K} \theta^{S_j} f^{S_j}(x_i^T)$$

where $\theta = [\theta^{S_1}, \theta^{S_2}, \theta^{S_2}, \ldots, \theta^{S_K}]^T$ represents a migration weight of each source model, a weight that minimizes a difference between two samples in a target center sample set is sought based on a smoothness assumption on the sample data of the target center, which is expressed as the following optimization problem:

$$\min_{\theta: \theta'e = 1, \theta \geq 0} \sum_{i,j=1}^{n_T} (H_i^S \theta - H_j^S \theta)^2 W_{ij}$$

where $\theta'$ is a transposition of $\theta$, e is a unit vector, and $W_{ij}$ indicates the similarity among samples;

the aforementioned optimization problem is transformed into:

$$\min_{\theta: \theta'e = 1, \theta \geq 0} \theta' H^{S'} L^T H^S \theta$$

where $H^S$ is a $n_T \times K$ matrix, and $L^T$ represents a graph Laplacian operator related to the target center, which is obtained by calculating according to $L^T = D - W$, where W is a similarity matrix of samples of the target center, and D is a diagonal matrix obtained by calculating according to $D_{ii} = \Sigma_{j=1}^{n_T} W_{ij}$, therefore, the optimization problem is transformed into a standard quadratic programming problem, which is solved to obtain a migration weight θ;

the target model calculation unit is arranged at the target center, obtains a sample pseudo label according to the migration weight θ, a terminal processor of the target model calculation unit trains the target cancer prognosis prediction model at the target center by utilizing the sample pseudo label, and transmits the trained target model back to the management center by a signal sender.

2. The multi-center synergetic cancer prognosis prediction system based on multi-source migration learning according to claim 1, wherein the system further comprises a model application process, which is arranged at the management center, receives the sample feature input by a user when setting the model parameter, calls the target model to perform cancer prognosis prediction, and presents a prediction result to the user.

3. The multi-center synergetic cancer prognosis prediction system based on multi-source migration learning according to claim 1, wherein the cancer prognosis prediction model adopts a logistic regression model, a support vector machine model, a decision tree model, a neural network model, or other models.

4. The multi-center synergetic cancer prognosis prediction system based on multi-source migration learning according to claim 1, wherein the similarity $W_{ij}$ among the samples is cosine similarity, Gaussian similarity or other models.

5. The multi-center synergetic cancer prognosis prediction system based on multi-source migration learning according to claim 1, wherein the sample data preprocessing method comprises missing value processing, dummy variable processing, normalization processing, and other processing.

6. The multi-center synergetic cancer prognosis prediction system based on multi-source migration learning according to claim 1, wherein the sample feature comprises demographic information, physiological parameters, cancer pathological examination information and other information extracted from an electronic medical record of a patient.

* * * * *